United States Patent
Huber et al.

(10) Patent No.: US 11,690,776 B2
(45) Date of Patent: Jul. 4, 2023

(54) VARIABLE COMPRESSION BODY ANCHOR

(71) Applicant: Massachusetts Institute of Technology, Cambridge, MA (US)

(72) Inventors: Meghan Huber, Salem, MA (US); James Hermus, Oregon, WI (US); Gabrielle Enns, Boston, MA (US); Neville Hogan, Sudbury, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 519 days.

(21) Appl. No.: 16/789,638

(22) Filed: Feb. 13, 2020

(65) Prior Publication Data
US 2021/0251839 A1    Aug. 19, 2021

(51) Int. Cl.
A61H 3/00    (2006.01)
A61F 2/60    (2006.01)
A61F 5/01    (2006.01)

(52) U.S. Cl.
CPC .................. *A61H 3/00* (2013.01); *A61F 2/60* (2013.01); *A61F 5/0104* (2013.01); *A61H 2003/007* (2013.01); *A61H 2201/0196* (2013.01); *A61H 2201/14* (2013.01); *A61H 2201/164* (2013.01); *A61H 2201/1645* (2013.01)

(58) Field of Classification Search
CPC ............ A61H 3/00; A61F 2/60; A61F 5/0104
See application file for complete search history.

(56) References Cited

U.S. PATENT DOCUMENTS

| | | | |
|---|---|---|---|
| 4,146,021 A | 3/1979 | Brosseau et al. | |
| 5,692,321 A | 12/1997 | Holstine | |
| 8,652,059 B2 | 2/2014 | Sano et al. | |
| 10,048,703 B1 | 8/2018 | Shaker et al. | |
| 2007/0027421 A1* | 2/2007 | Nobbe | A61F 5/0113 128/882 |
| 2015/0018733 A1* | 1/2015 | Ben-Meir | A41D 13/065 602/6 |
| 2016/0235578 A1* | 8/2016 | Romo | A61F 5/0127 |

(Continued)

FOREIGN PATENT DOCUMENTS

WO    WO 2017/160751    9/2017
WO    WO 2019/084448    5/2019

OTHER PUBLICATIONS

Akiyama, et al., "Measurement of Contact Behavior Including Slippage of Cuff When Using Wearable Physical Assistant Robot;" IEEE Transaction on Neural Systems and Rehabilitation Engineering, vol. 24, No. 7; Jul. 2016; 10 Pages.

(Continued)

*Primary Examiner* — Jerrah Edwards
*Assistant Examiner* — Aren Patel
(74) *Attorney, Agent, or Firm* — Daly, Crowley, Mofford & Durkee, LLP

(57) ABSTRACT

In some embodiments, a body anchor for supporting an assistive device can include: a cuff to exert a compression force on a body part of a user; and one or more tensile elements having first ends and second ends. The first ends of the tensile elements can be configured to be attached to the assistive device. The second ends of the tensile elements can be arranged about the cuff to cause the compression force to vary in proportion to a load exerted by the assistive device.

11 Claims, 9 Drawing Sheets

(56) References Cited

U.S. PATENT DOCUMENTS

| | | | |
|---|---|---|---|
| 2016/0252110 A1* | 9/2016 | Galloway | F15B 15/103 60/327 |
| 2017/0202724 A1* | 7/2017 | De Rossi | A61H 3/00 |
| 2018/0055713 A1* | 3/2018 | Cromie | A63B 24/0087 |
| 2019/0030708 A1* | 1/2019 | Holgate | A62B 35/0018 |
| 2019/0150530 A1 | 5/2019 | Basta et al. | |

OTHER PUBLICATIONS

Bae, et al., "A Soft Exosuit for Patients with Stroke: Feasibility Study with a Mobile Off-Board Actuation Unit;" 2015 IEEE International Conference on Rehabilitation Robotics; Aug. 11, 2015; 9 Pages.

Chiri, et al., "On the Design of Ergonomic Wearable Robotic Devices for Motion Assistance and Rehabilitation;" 34$^{th}$ Annual International Conference of the IEEE EMBS; Aug. 28, 2012; 4 Pages.

Choi, et al., "Exo-Wrist: A Soft Tendon-Driven Wrist-Wearable Robot with Active Anchor for Dart-Throwing Motion in Hemiplegic Patients;" IEEE Robotics and Automation Letters, vol. 4, No. 4; Oct. 2019; 8 Pages.

Collins, et al., "Reducing the Energy Cost of Human Walking Using an Unpowered Exoskeleton;" Nature, vol. 522; Jun. 11, 2015; 15 Pages.

Folgheraiter, et al., "Measuring the Improvement of the Interaction Comfort of a Wearable Exoskeleton: A Multi-Modal Control Mechanism Based on Force Measurement and Movement Prediction;" International Journal of Social Robotics; Aug. 2012; 33 Pages.

Kermavnar, et al., "Computerized Cuff Pressure Algometry as Guidance for Circumferential Tissue Compression for Wearable Soft Robotic Applications: A Systematic Review;" Soft Robotics, vol. 5, No. 1; Feb. 2018; 16 Pages.

Kim, et al., "Reducing the Metabolic Rate of Walking and Running with a Versatile, Portable Exosuit;" Science, vol. 365; Aug. 16, 2019; 6 Pages.

Reports and Data, "Exoskeleton Market to Reach USD 4.00 Billion By 2026;" Reports and Data; May 22, 2019; 4 Pages.

Schiele, et al., "Influence of Attachment Pressure and Kinematic Configuration on pHRI with Wearable Robots;" Applied Bionics and Biomechanics, vol. 6, No. 2; Jun. 2009; 18 Pages.

Sposito, et al., "Towards Design Guidelines for Physical Interfaces on Industrial Exoskeletons: Overview on Evaluation Metrics;" Wearable Robotics: Challenges and Trends; Oct. 2018; 4 Pages.

Tao, "Mechanical Bracing Solutions to Decrease Tibial Slippage of Anklebot," Massachusetts Institute of Technology Libraries; Jun. 30, 2010; 19 Pages.

Yandell, et al., "Physical Interface Dynamics Alter How Robotic Exosuits Augment Human Movement: Implications for Optimizing Wearable Assistive Devices;" Journal of NeuroEngineering and Rehabilitation; vol. 14, No. 40; May 18, 2017; 11 Pages.

PCT International Search Report and Written Opinion dated May 26, 2021 for International Application No. PCT/US2021/016802; 13 pages.

International Preliminary Report on Patentability dated Aug. 25, 2022 for Application No. PCT/US2021/016802; 8 Pages.

* cited by examiner

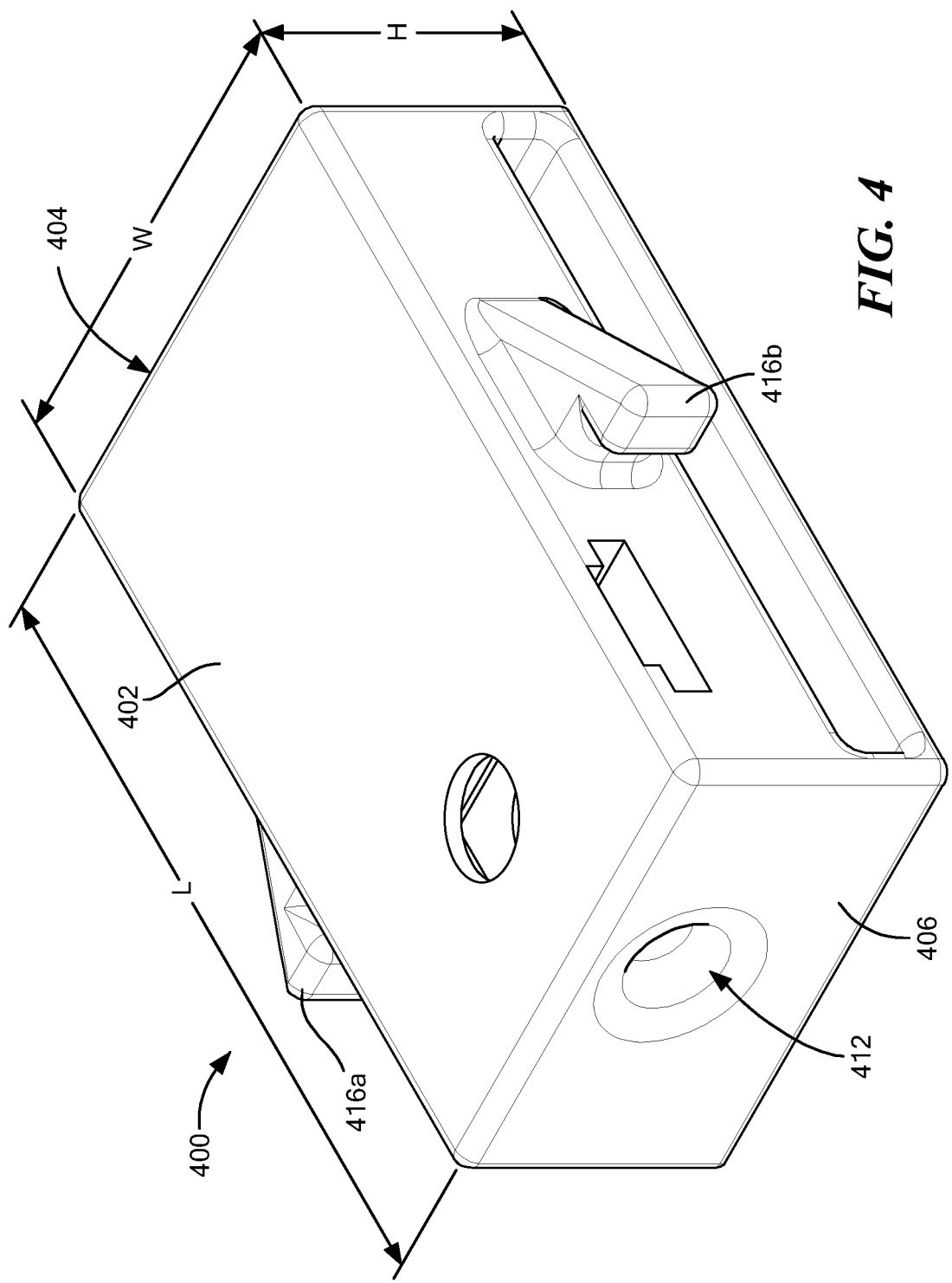

VARIABLE COMPRESSION BODY ANCHOR

STATEMENT REGARDING FEDERALLY SPONSORED RESEARCH

This invention was made with government support under Grant No. BCS1724135 and IIS1637824 awarded by the National Science Foundation (NSF). The government has certain rights in the invention.

BACKGROUND

Assistive devices—such as prostheses, braces, exoskeletons, robotic devices, etc.—have potential to increase the functionality of individuals with motor impairments. Before such devices can be practically used in everyday life, challenges associated with anchoring them to a user's body need to be addressed. Some assistive devices are anchored to the body by means of a cuff. An unbalanced shear force exerted on a body anchor by an assistive device can result in motion of the body anchor with respect to the body and, in turn, between the body anchor and the assistive device. Such relative motion can prevent the transmission of force from the assistive device, rendering the device ineffective. For example, relative movement or "slippage" of a body anchor can reduce the user's ability to control a prosthetic limb or appendage. Furthermore, such cuff slippage can create blisters and abrasions on the skin, making the assistive devices uncomfortable for the user to wear over time.

Current body-anchor systems employ various approaches to prevent unwanted slippage. For example, a cuff may be designed to have a relatively high constant compression around a user's limb. As another example, high-friction materials have been used within body anchors. As yet another example, cuffs have been anchored to other body parts (e.g., to other limb segments across other joints) to support the cuff. Each of these approaches can increase discomfort to the user and/or fail to entirely prevent cuff slippage. The later issue is particularly problematic due to limb geometry (i.e., tendency of limbs to decrease in circumference towards their distal end) in that the amount of cuff slippage can be amplified as the cuff slips.

SUMMARY

According to one aspect of the present disclosure, a body anchor for supporting an assistive device can include: a cuff to exert a compression force on a body part of a user; and one or more tensile elements having first ends and second ends, the first ends of the tensile elements configured to be attached to the assistive device, the second ends of the tensile elements arranged about the cuff to cause the compression force to vary in proportion to a load exerted by the assistive device.

In some embodiments, the cuff can include a synthetic rubber material or an elastic fiber material. In some embodiments, the assistive device may include a lower limb exoskeletal device, wherein the cuff is sized to be worn over a leg of the user. In some embodiments, the tensile elements can be arranged about the cuff to counterbalance the load exerted by the assistive device.

In some embodiments, the one or more tensile elements may include: a first tensile element encircling the cuff in a first direction; and a second tensile element encircling the cuff in a second direction opposite from the first direction. In some embodiments, the body anchor can include a guide fixedly attached to the cuff and having a first channel, a second channel, a first anchor point, and a second anchor point, wherein the first tensile element passes through the first channel, encircles the cuff in the first direction, and is attached at its second end to the first anchor point, and wherein the second tensile element passes through the second channel, encircles the cuff in the second direction, and is attached at its second end to the second anchor point. In some embodiments, the guide can include: a first opening in a first end of an enclosure; and second and third openings in a second end of the enclosure opposite from the first end, wherein the first channel extends from the first opening to the second opening and the second channel extends from the first opening to the third opening.

In some embodiments, the one or more tensile elements may have loops at the second ends, wherein the one or more tensile elements pass through the loops and wrap around the cuff. In some embodiments, the cuff can include a first end having a first plurality of openings and a second end having a second plurality of openings, wherein the one or more tensile elements are arranged through the first and second plurality of openings to force the first and second cuff ends together in proportion to the load exerted by the assistive device. In some embodiments, the one or more tensile elements may be laced through the first and second plurality of openings.

In some embodiments, the cuff can include a non-isotropic material formed into a cylindrical structure, wherein the one or more tensile elements are arranged about the cylindrical structure to cause the circumference of the cylindrical structure to vary in proportion to a load exerted by the assistive device. In some embodiments, the cuff can include a first helically wound braid of fibers and a second helically wound braid of fibers, the first and second helically would braids of fibers being wound in opposite directions about the cylindrical structure.

According to one aspect of the present disclosure, a body anchor for supporting a load can include: a cuff wearable over a limb of a user; and a means for converting a shear force acting on the cuff due to a load into a compression force that increases shear friction between the cuff and the limb in response to an increase in the load.

In some embodiments, the cuff can include a synthetic rubber material or an elastic fiber material. In some embodiments, the load may include a lower limb exoskeletal device, wherein the cuff is sized to be worn over a leg of the user. In some embodiments, the means for converting the shear force acting on the cuff due to the load to the compression force can include one or more tensile elements connecting the load to the cuff.

In some embodiments, the one or more tensile elements may be arranged about the cuff to counterbalance the load. In some embodiments, the one or more tensile elements can include: a first tensile element encircling the cuff in a first direction; and a second tensile element encircling the cuff in a second direction opposite from the first direction. In some embodiments, the body anchor can include a means for attaching the one or more tensile elements to the cuff and a means for guiding the one or more tensile elements about the cuff.

BRIEF DESCRIPTION OF THE DRAWINGS

Various objectives, features, and advantages of the disclosed subject matter can be more fully appreciated with reference to the following detailed description of the disclosed subject matter when considered in connection with the following drawings, in which like reference numerals identify like elements.

FIG. 4 is perspective view of a guide structure that can be used with a variable compression body anchor, according to some embodiments of the present disclosure.

The drawings are not necessarily to scale, or inclusive of all elements of a system, emphasis instead generally being placed upon illustrating the concepts, structures, and techniques sought to be protected herein.

DETAILED DESCRIPTION

Figure 1:
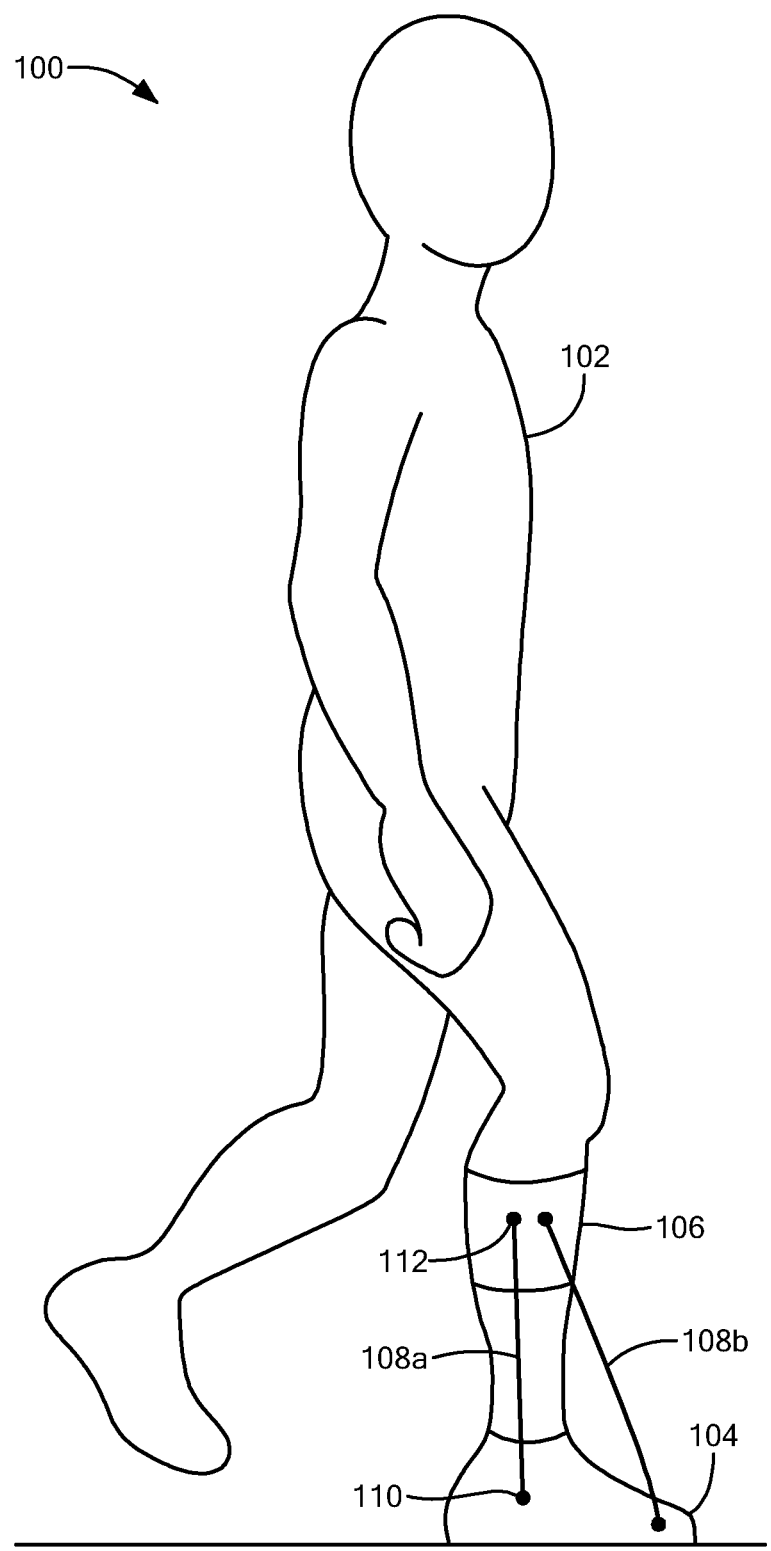
FIG. 1 is a diagram illustrating an environment in which a variable compression body anchor can be used, according to some embodiments of the present disclosure.

FIG. 1 shows an illustrative environment 100 in which a variable compression body anchor may be employed. A user 102 may wear an assistive device 104 such as a prosthetic device, a brace, an exoskeletal device, a robotic device, or other type of mechanical device that provides assistance to the user. User 102 can include a human person, an animal, or other user of assistive device 104. The assistive device 104 can be anchored to the user's body by means of a body anchor 106. Body anchor 106 can be disposed over or around a part of the user's body and configured to support the load exerted by the assistive device 104. For example, as shown in FIG. 1, body anchor 106 may be worn over a user's leg to provide support for an exoskeletal device 104 used for gait assistance. Embodiments of variable compression body anchors described herein can be attached to other parts of a user's body, such as a shoulder, an arm, a torso, etc. and can be used in conjunction with a wide array of assistive devices.

Assistive device 104 may be attached to body anchor 106 via one or more tensile elements 108a, 108b, etc. (108 generally). In some embodiments, a tensile element 108a can have a first end 110 attached to assistive device 104 and a second end 112 attached to body anchor 106. While two tensile elements 108 are shown in FIG. 1, it should be understood that different numbers of tensile elements can be used in different embodiments disclosed herein. Tensile elements 108 can include wires or woven straps formed from a metal, synthetic fiber (e.g., nylon, Kevlar, Spectra, etc.), or other structure or material with a tensile strength, stiffness, and inextensibility sufficient to withstand the load exerted by assistive device 104.

Body anchor 106 may held in place as a result of friction between the user's body (e.g., the user's skin) and the body anchor 106. In some embodiments, body anchor 106 can include a compression material. Non-limiting examples of compression materials include synthetic rubber materials such as neoprene and elastic fiber materials such as spandex. The compression material may be formed as a cuff that can be worn over a user's limb. That is, the dimensions of the cuff (e.g., the length and circumference of the cuff) may be selected based on the particular body part over which it is intended to be worn and/or based on the physical characteristics of an intended user or population of users. In general, the cuff can be made of any material that allows compressive forces to be applied onto the limb needed to accommodate the range of shear loads applied.

As discussed in greater detail below, according to various embodiments, tensile elements 108 and body anchor 106 can be arranged together to convert the shear force exerted by the assistive device 104 into a compression force that increases shear friction between the user's body and the body anchor 106. That is, according to the present disclosure, the compressive force of a body anchor 106 can vary in proportion to the load of an assistive device 104. It is appreciated herein that the load exerted by an assistive device 104 on a body anchor 106 can vary with movement of the user's body. For example, in the case of a foot-worn device anchored to the user's leg (such as illustrated in FIG. 1), load on the anchor 106 can change when the user's ankle rotates or flexes. Similarly, for lower-limb exoskeletal devices used for gait assistance, load on the body anchor 106 can vary as the user walks or runs.

Figure 2:
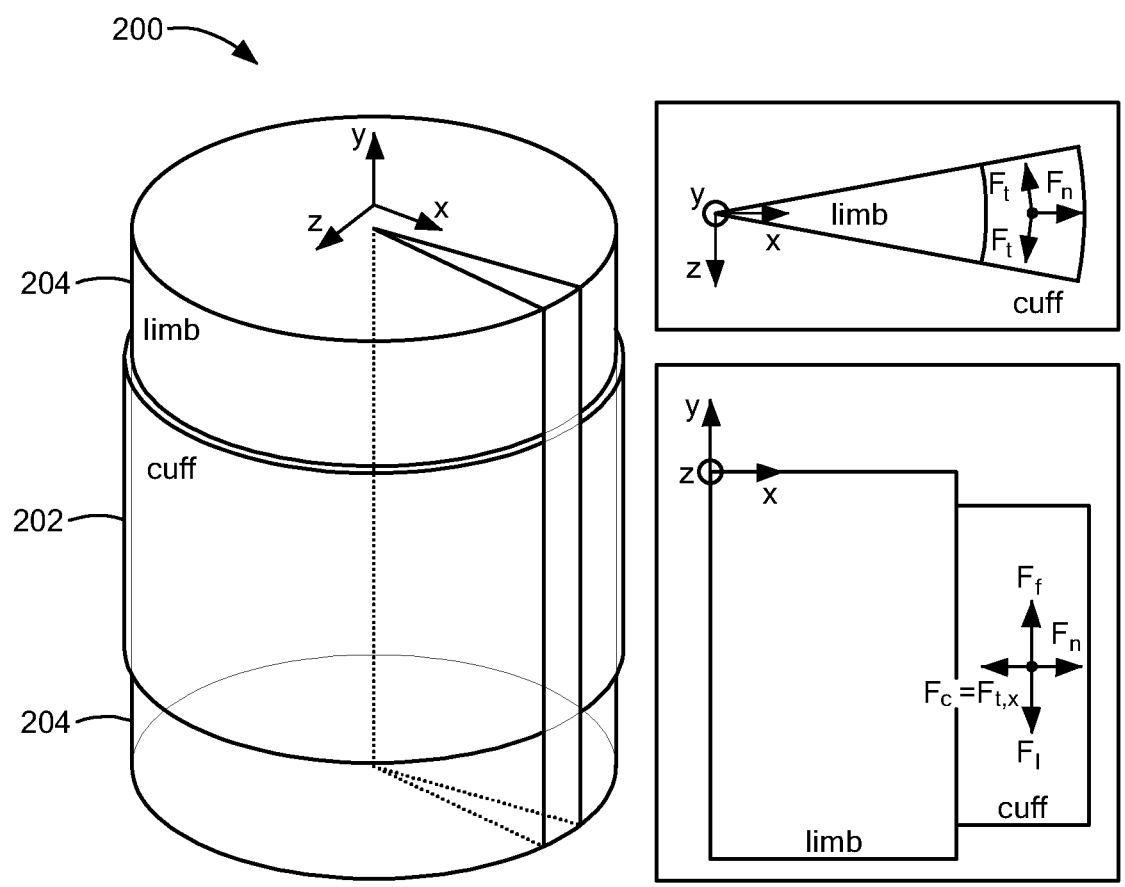
FIG. 2 is a free body diagram of a body anchor, according to some embodiments of the present disclosure.

FIG. 2 is a free body diagram 200 of the interface between a user's limb 202 and a body anchor 204 disposed there around. The free body diagram 200 shows: $F_l$, load applied to the anchor 204 from an assistive device, such as device 104 of FIG. 1; $F_f$, frictional force between the limb 202 and the body anchor 204; $F_t$, tension of the body anchor 204; $F_c$, compression force of the body anchor 204 on the limb 202 resulting from $F_t$; and $F_n$, normal force of the limb 202 on the body anchor 204.

As shown in FIG. 2, $F_f$, the friction between the limb 202 and the anchor 204 depends on the compression force, $F_c$. If a Coulomb friction model is assumed, it can be seen that friction force, $F_f$, is proportional to compression force, $F_c$, such that $F_f = \mu F_c$ where $\mu$ is the coefficient of friction.

Some existing systems are designed to maximize the load which can be applied, subject to the constraint that the load does not cause cuff movement nor excessive discomfort to the user. To achieve these objectives, existing systems may (a) increase the coefficient of friction, $\mu$, by using a material with a high coefficient of friction between the body anchor and the limb; and/or (b) increase $F_c$ by compressing the anchor as much as can be tolerated by the user. However, it is appreciated herein that the load applied to the body anchor is not constant for most applications (e.g., lower limb exoskeletal devices for gait assistance). As load, $F_l$, decreases, the compression force, $F_c$, required to compensate for the load also decreases. Any time $F_l$ is less than its maximum value, a conventional body anchor with constant compression would exert unnecessarily large forces on the user, which can cause discomfort, compromise circulation, or even result in soft tissue injury. At the same time, decreasing $F_c$ reduces the maximum $F_l$ and hence, assuming $F_c$ is constant, also reduces the amount of assistance that can be provided to the user without causing the body anchor to slip.

Embodiments of the present disclosure provide for a variable compression body anchor 204 wherein $F_c$, the frictional force between the limb 202 and the body anchor 204, varies in proportion to, $F_l$, the load applied to the anchor 204 from an assistive device. As such, embodiments of the present disclosure can reduce the amount of time that a user experiences large compressive forces, while still allowing the maximum value of $F_l$ to be sufficiently high to prevent slippage of the body anchor. It is appreciated herein that varying shear friction at the body anchor in response to the shear load of the assistive device can reduce (and ideally eliminate) slippage while also reducing (and ideally minimizing) user discomfort. Further, embodiments of the present disclosure can reduce slippage by conforming to changes in limb shape. Moreover, by varying compressive forces, embodiments of the present disclosure can result in cyclic compression and relaxation (due to varying device loading) having a peristaltic pumping action which could potentially enhance circulation in the limb rather than compromise it by applying a constant and excessive compression.

Figure 3:
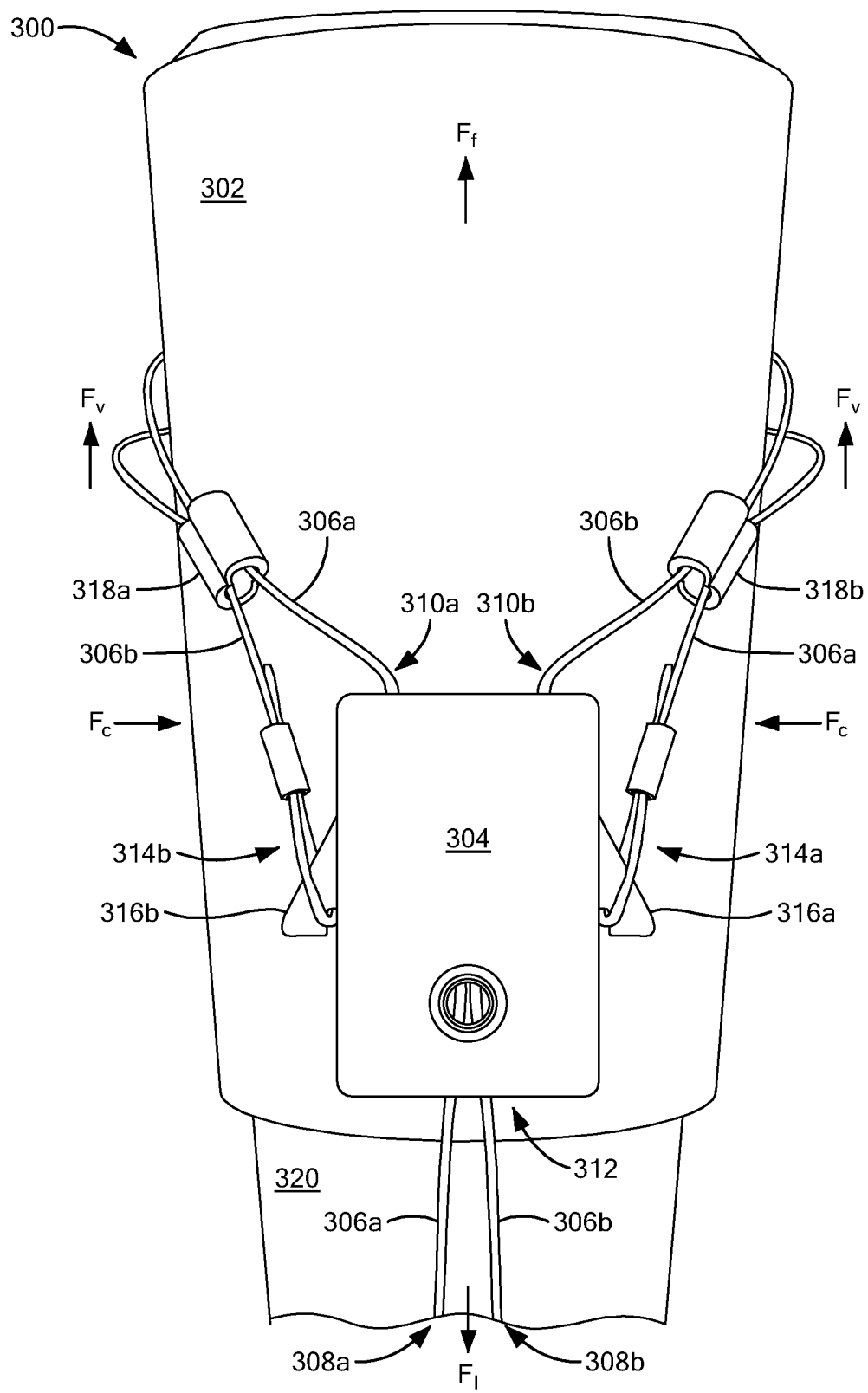
FIG. 3 is a schematic view of a variable compression body anchor, according to some embodiments of the present disclosure.

Turning to FIG. 3, according to some embodiments of the present disclosure, a variable compression body anchor 300 can include a cuff 302, a guide structure 304 fixedly attached thereto, and a pair of tensile elements 306a, 306b (306 generally). The cuff 302 may be worn over a user's limb 320 or other body part and may exert a compression force, $F_c$, thereon. Cuff 302 may include a compression material such as a synthetic rubber material or an elastic fiber material.

Guide structure (or "guide") 304 may be rigid structure designed to serves at least two purposes: (1) it is the interface through which the tensile elements 306 are attached to the cuff 302 and (2) it "guides" or positions the tensile elements 306 such that it acts as a loop closure point for the loops created by the tensile elements wrapped around the limb (similar to a honda knot used on a lasso). In some embodiments, guide 304 can have a box-like shape. As shown in FIG. 3, guide 304 can include a first opening 310a located along one side of the rectangular structure (the top side in FIG. 3), a second opening 310b also located along the top side of the rectangular structure, and a third opening 312 located along an opposite side of the rectangular structure (the bottom side in FIG. 3). Guide 304 can include one or more channels through which the tensile elements 306 can pass. In particular, guide 304 can include a first channel extending from first opening 310a to third opening 312, and a second channel extending from second opening 310b to third opening 312. A detailed example of a guide structure 304 is shown in described below in the context of FIGS. 4 and 4A. Guide 304 can be attached to cuff 302 using, for example, a silicone sealant or other glue, sewing, with a fastener.

The tensile elements 306a, 306b may have respective first ends 308a, 308b (308 generally) attached to an assistive device (not shown) and respective second ends 314a, 314b (314 generally) attached to the guide structure 304. In more detail, first tensile element 306a can pass through the first channel of guide 304 (i.e., a channel extending from first opening 310a to third opening 312), wrap around the outer circumference of cuff 302, and attach to a first anchor point 316a of the guide 304. Second tensile element 306b can pass through the second channel of guide 304 (i.e., a channel extending from second opening 310b to third opening 312), wrap around the outer circumference of cuff 302, and attach to a second anchor point 316b of the guide 304. In some embodiments, the two tensile elements 306a, 306b can wrap in opposite directions around the cuff 302. For example, as shown in FIG. 3, first tensile element 306a can wrap in a clockwise direction around cuff 302 and second tensile element 306b can wrap in a counterclockwise direction around cuff 302. In this arrangement, tensile elements 306 can cause compression force, $F_c$, to vary in proportion to a load, $F_l$, exerted by the assistive device. For example, as the load applied to the first ends 308 of the tensile elements, $F_l$, increases, the tensile elements tighten around the limb 320, increasing the compressive force, $F_c$. Tensile elements 306 can include metal or synthetic fiber, such as discussed above in the context of FIG. 1.

The arrangement of tensile elements 306 shown in FIG. 3 is merely one example. In general, tensile elements 306 may be routed in any fashion such that they do not interfere with each other (i.e., such that each tensile element 306 can pass freely through guide 304 and around cuff 302). While the embodiment of FIG. 3 includes two tensile elements 306a, 306b, it is appreciated that other numbers of tensile elements can be used.

In some embodiments, the body anchor 300 can include one or more wire casings 318a, 318b, etc. (318 generally) attached to the cuff 302 to maintain a certain configuration of the tensile elements 306 relative to the cuff. Various shapes and sizes of wire casings 318 can be used. The casings 318 can be made from a low friction material such that the tensile elements 306 can freely move through them.

In some embodiments, tensile elements 306 may be arranged about the cuff 302 to counterbalance downward shear forces acting on the guide 304. That is, the tensile elements 306 can be arranged such that there is minimal net downward force on the guide 304, thereby allowing the guide 304 to properly serve as a loop closure point. For example, as shown in FIG. 3, tensile elements 306a, 306b may be routed at least partially above the guide structure 304 so as to produce an upwardly-directed force component, $F_v$, on the guide 304. Further, the second ends of the wires 314 can be attached to the guide 304 at an upward angle, such as using wing-shaped anchor points 316, as illustrated in FIG. 3.

Figure 4A:
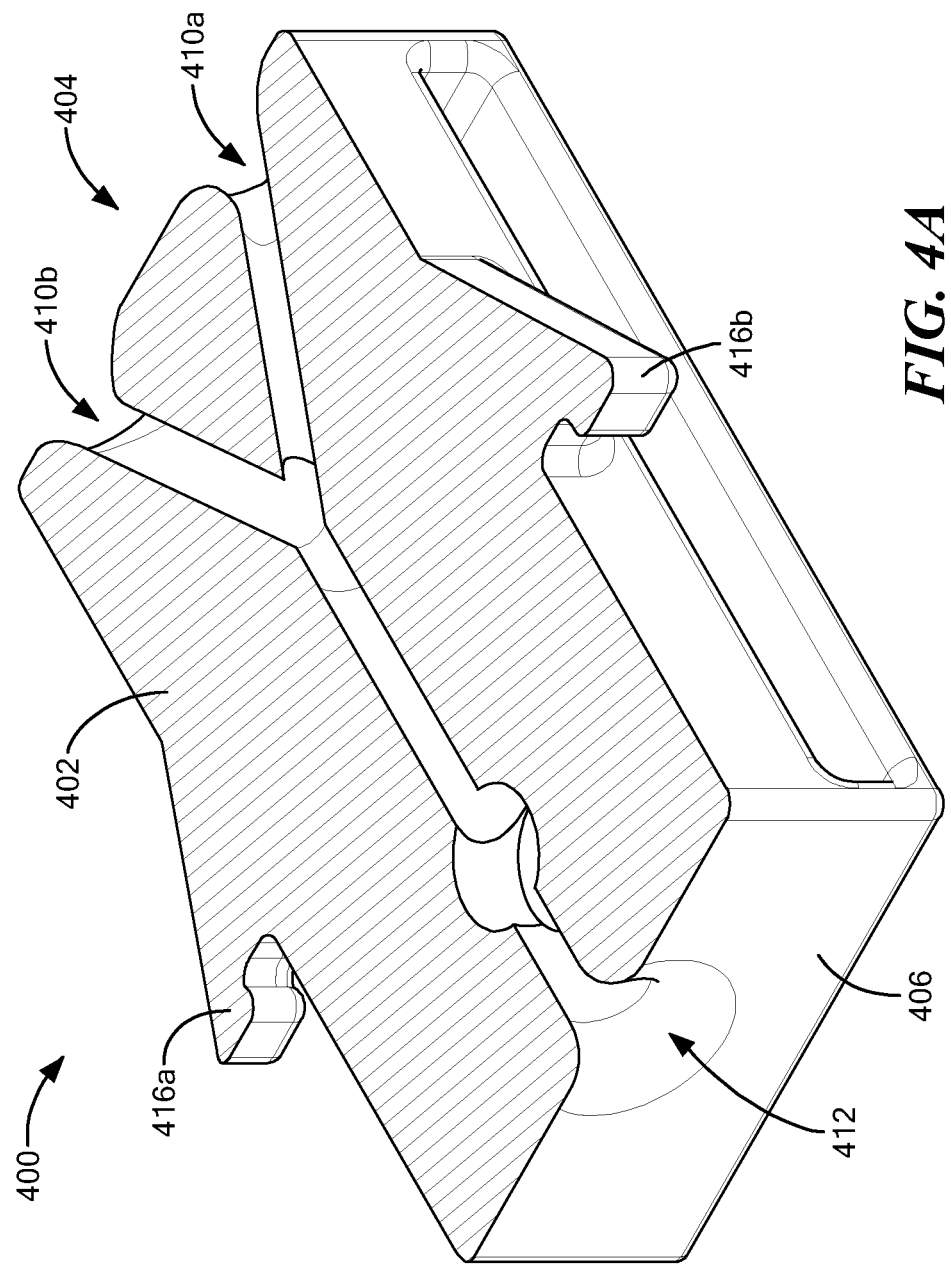
FIG. 4A is a sectional view of the guide structure shown in FIG. 4.

FIGS. 4 and 4A show an example of a guide structure 400 that can be used with a variable compression body anchor, according to some embodiments of the present disclosure. The illustrative guide structure (or "guide") 400, which may be the same as or similar to guide 304 of FIG. 3, includes a rigid rectangular structure 402 having first and second openings 410a, 410b (FIG. 4A) located along a first side 404 of the structure 402, and a third opening 412 located along a second side 406 of the structure opposite from the first side 404. As shown in FIG. 4A, guide 400 includes Y-shaped channels through which a pair of tensile elements (e.g., tensile elements 306a, 306b of FIG. 3) can pass. In particular, guide 400 includes a first channel extending from first opening 410a to third opening 412, and a second channel extending from second opening 410b to third opening 412.

The illustrative guide structure 400 further includes two anchor points 416a, 416 whereupon the two tensile elements can be attached. As illustrated in FIGS. 4 and 4A, the anchor points 416 can be provided as wing-shaped protrusions on opposite sides of the rectangular structure 402. The anchor points 416 can be formed as part of the guide structure 400 (e.g., using a 3D printing technique) or can be attached thereto using a glue or fastener.

As illustrated in FIG. 4, rectangular structure 402 can have a width W, a length L, and a height H. In some embodiments, W may be about 33 mm, L may be about 450 mm, and H may be about 17.5 mm.

The guide structure 400 shown in FIGS. 4 and 4A is merely one example. In general, a guide structure according to the present disclosure can have any shape or design such that it permits tensile elements to move unimpeded through guide. For example, a guide structure may be designed such that there is relatively low friction between the tensile element and the guide and no sharp corners for the tensile elements to move over. Moreover, a guide structure may be designed such that, as the tensile elements move through the guide, they apply a minimal downward force on the guide. In some embodiments, the tensile elements can move through the guide at angles close or if possible equal to the vertical direction. In some embodiments, the tensile elements may be attached on the guide in such a way that they apply an upward force on the guide to counteract a potential downward force they may apply by moving within the guide. For instance, the tensile elements can be attached at an angle close if not equal to the vertical direction, such as shown in FIG. 3.

Figure 5:
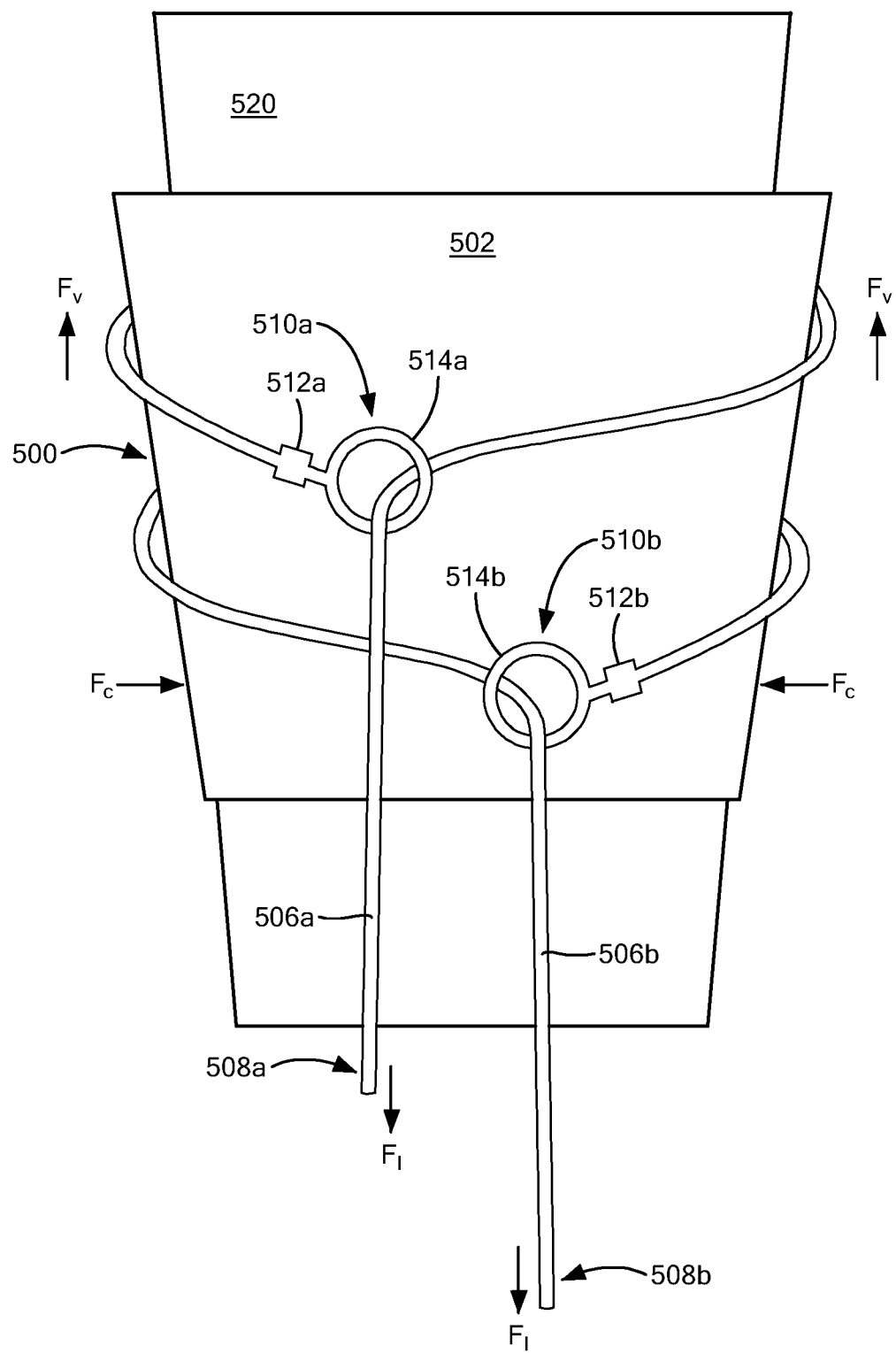
FIG. 5 is a schematic view of another variable compression body anchor, according to some embodiments of the present disclosure.

FIG. 5 shows a variable compression body anchor 500 according to another embodiment of the present disclosure. The illustrative body anchor 500 can include a cuff 502 and one or more tensile elements 506a, 506b, etc. (506 generally). The cuff 502, which may be the same as or similar to cuff 302 of FIG. 3, can exert a compression force, $F_c$, on a user's limb 520 or other body part.

Tensile elements 506 may have respective first ends 508a, 508b (508 generally) attached to an assistive device (not shown), and respective second ends 510a, 510b (510 generally) attached to the cuff 502. In particular, tensile elements 506a, 506b can have, at their second ends 508, respective attachment portions 512a, 512b (512 generally) fixedly attached to the cuff 502, and respective loops 514a, 514b (514 generally). Elements 512 and 514 can collectively serve a similar function as guide structure 304 of FIG. 3. The attachment portions 512 can be affixed to the cuff 502 using, for example, sealant, glue, sewing (either directly or indirectly through another piece of material), or with a fastener. The tensile elements 506 can pass through the loops 514 and wrap around the outer circumference of cuff 502, as shown. In this arrangement, as the load, $F_l$, applied to the first ends 508 of the tensile elements increases, the tensile elements tighten around the limb 520, increasing the compressive force, $F_c$.

Tensile elements 506 can include metal or synthetic fiber, such as discussed above in the context of FIG. 1. While the embodiment of FIG. 5 includes two tensile elements 506a, 506b, other numbers of tensile elements can be used.

Tensile elements 506 may be arranged about the cuff 502 to produce an upward force component, $F_v$, acting on the guide elements 512, 514 that counterbalances downward shear forces on elements 512, 514. This can ensure that the tensile elements 506 properly move through the loops 514.

Figure 6:
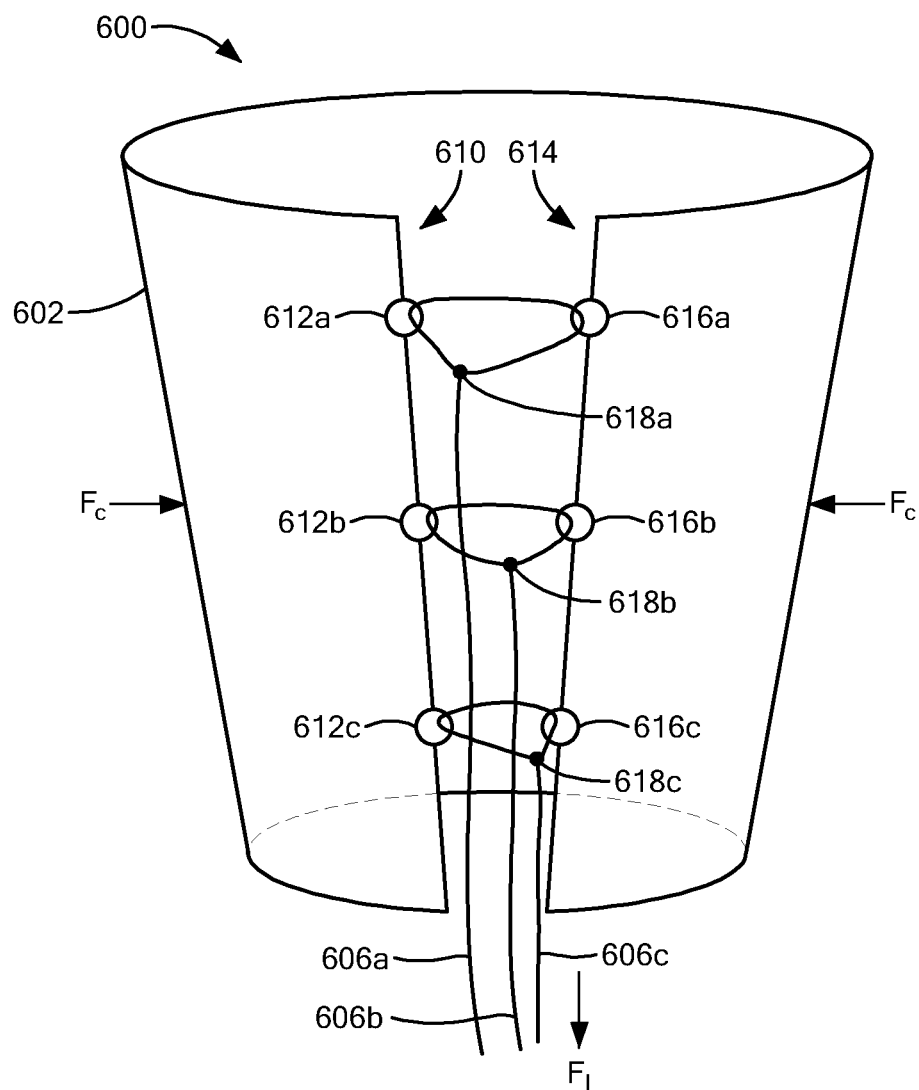
FIG. 6 is a schematic view of another variable compression body anchor, according to some embodiments of the present disclosure.

FIG. 6 shows a variable compression body anchor 600 according to another embodiment of the present disclosure. The illustrative body anchor 600 includes a cuff 602 and a plurality of tensile elements 606a, 606b, 606c, etc. (606 generally). The cuff 602 can include a first end 610 having first openings 612a, 612b, 612c, etc. (612 generally) and an opposing second end 614 having second openings 616a, 616b, 616c, etc. (616 generally). Each of the first openings 612 may be in general horizontal alignment with a corresponding one of the second openings 616 when the cuff 602 is worn around a user's limb. Each of the tensile elements 606 can pass through one of the first openings 612 openings and a corresponding one of the second openings 614. The top ends of tensile elements 606a, 606b, 606c (i.e., the ends that pass through openings 612, 616) can be connected together at respective points 618a, 618b, 618c using, for example, knots or a lasso-like arrangement. The free ends of the tensile elements 606 may be attached to an assistive device load, $F_l$. In this arrangement, as the load, $F_l$, increases, the tensile elements 606 will tend to pull the two ends of the cuff 610 and 614 together, increasing the compressive force, $F_c$. While the illustrative body anchor 600 of FIG. 6 is shown having three tensile elements 606 and three corresponding openings in each end of the cuff 610, 614, it is appreciated that different numbers of tensile elements and end-openings can be used in other embodiments.

Figure 7:
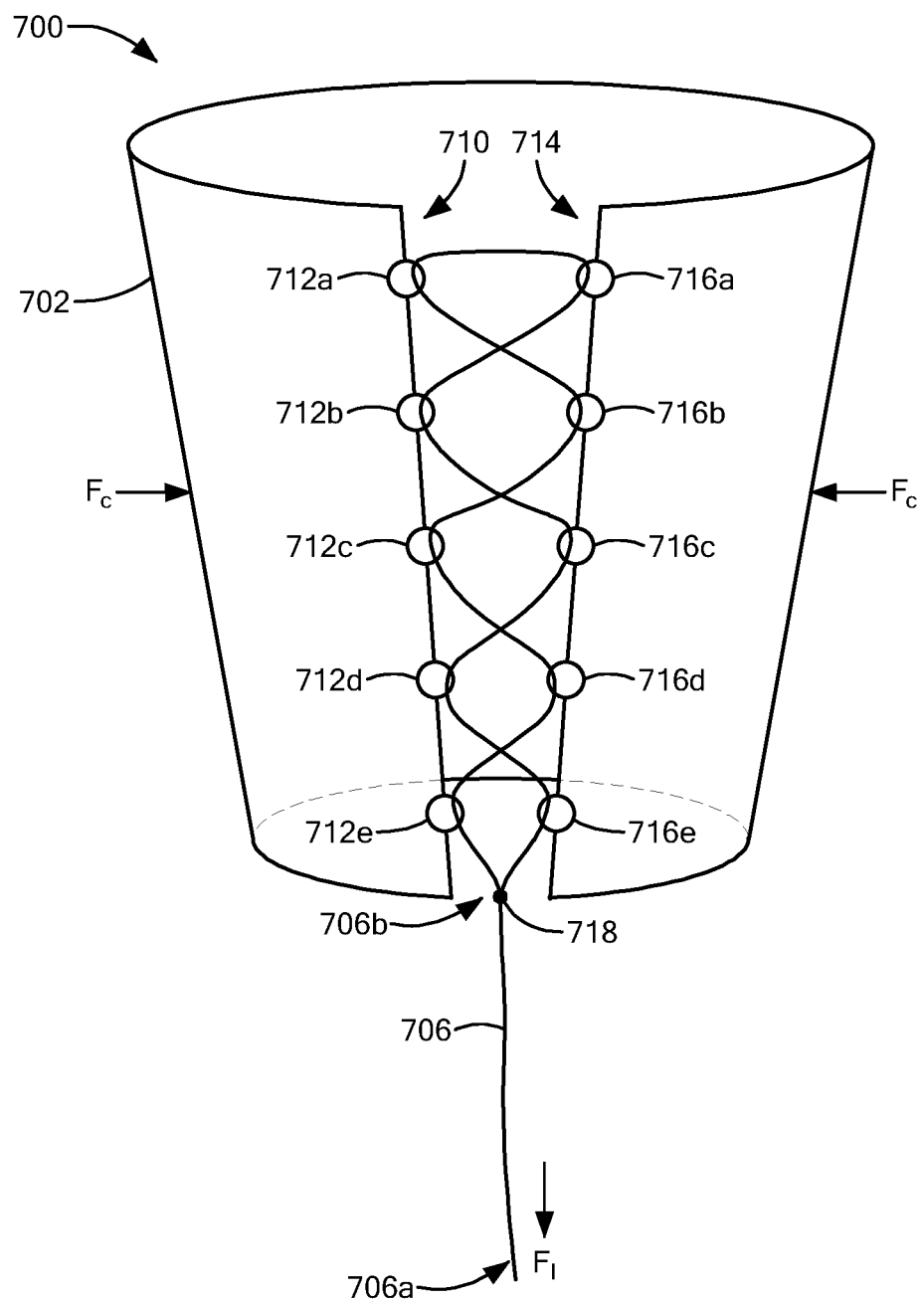
FIG. 7 is a schematic view of another variable compression body anchor, according to some embodiments of the present disclosure.

FIG. 7 shows a variable compression body anchor 700 according to another embodiment of the present disclosure. The illustrative body anchor 700 includes a cuff 702 and a tensile element 706. The cuff 702 includes a first end 710 having first openings 712a-712e (712 generally) and an opposing second end 714 having second openings 716a-716e (716 generally). A first end (or "free end") 706a of the tensile element 706 may be attached to an assistive device load, $F_l$. A second end 706b of the tensile element can alternately pass through ones of the first openings 712 and ones of the second openings 716 in a laced pattern and be attached to the free end 706a at point 718 using, for example, a knot, lasso-like arrangement, or other attachment means. In this arrangement, as the load, $F_l$, increases, the tensile element 706 will tend to pull the two ends of the cuff 710 and 714 together, increasing the compressive force, $F_c$. While the illustrative body anchor 700 of FIG. 7 is shown having a single tensile element 706, additional tensile elements 706 may be used according the general concept sought to be protected. Likewise, while body anchor 700 is shown as having five openings in each end of the cuff 710, 714, other numbers of end-openings can be provided.

Figure 8:
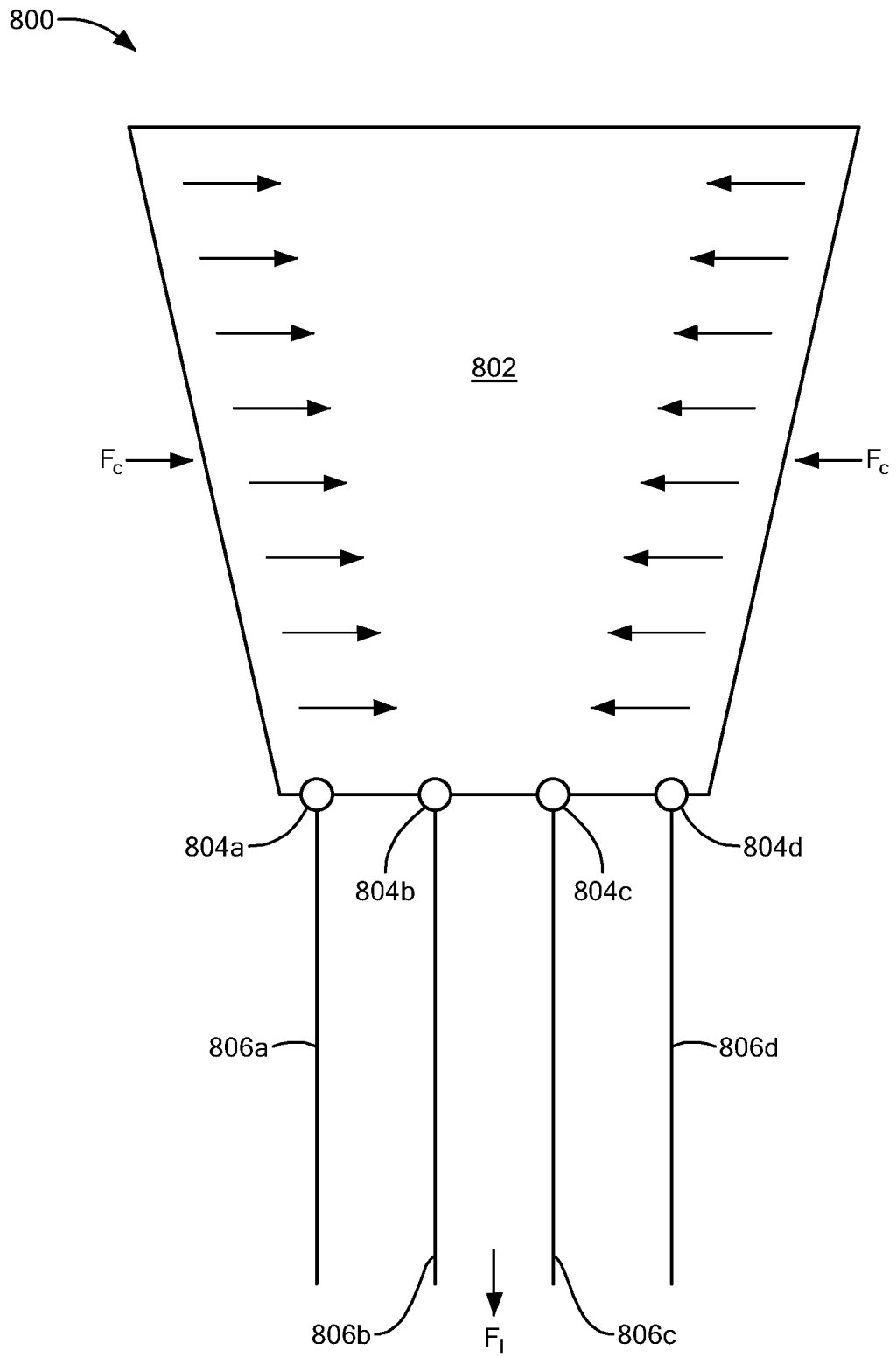
FIG. 8 is a schematic view of another variable compression body anchor, according to some embodiments of the present disclosure.

Turning to FIG. 8, according to another embodiment of the present disclosure, a variable compression body anchor 800 can include a compression material 802 formed into a cylindrical structure and one or more tensile elements 806a-806d (806 generally) attached to a bottom edge thereof. Tensile elements 806 can be attached using, for example, a sealant or other glue, sewing, knots, or other fastening means. In some embodiments, tensile elements 806 can be woven together with the compression material 802. For example, strands of fiber in the compression material 802 can continue downward to form tensile elements 806 or to be attached thereto. Then pulling on the strings would still cause the system to tighten. The compression material may include a non-isotropic material such as opposing helically wound braids of fibers (e.g., a first helically wound braid of fibers wound in a clockwise direction about the cylindrical structure and a second helically wound braid of fibers wound in a counterclockwise direction about the cylindrical structure). The free ends of the tensile elements 806 may be attached to an assistive device load, $F_l$. As the load, $F_l$, increases, the tensile elements 806 pull down on the compression material 802 causing it to lengthen and to decrease in circumference. Thus, the compressive force, $F_c$, exerted by the body anchor 700 tends to increase with load, $F_l$.

It is to be understood that the disclosed subject matter is not limited in its application to the details of construction and to the arrangements of the components set forth in the following description or illustrated in the drawings. The disclosed subject matter is capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods, and systems for carrying out the several purposes of the disclosed subject matter. Therefore, the claims should be regarded as including such equivalent constructions insofar as they do not depart from the spirit and scope of the disclosed subject matter.

Although the disclosed subject matter has been described and illustrated in the foregoing exemplary embodiments, it is understood that the present disclosure has been made only by way of example, and that numerous changes in the details of implementation of the disclosed subject matter may be made without departing from the spirit and scope of the disclosed subject matter.

The invention claimed is:

1. A body anchor for supporting an assistive device, the body anchor comprising:
    a cuff to exert a compression force on a body part of a user; and
    one or more tensile elements having first ends and second ends, the first ends of the tensile elements configured to be attached to the assistive device, the second ends of the tensile elements arranged about the cuff to cause the compression force to vary in proportion to a load exerted by the assistive device, wherein the one or more tensile elements comprise a first tensile element encircling the cuff in a first direction and a second tensile element encircling the cuff in a second direction opposite from the first direction, wherein the tensile elements are arranged to cause the compression force to increase at multiple points around a circumference of the cuff as the load increases, including at diametrically opposite points of the circumference; and
    a rigid guide structure fixedly attached to the cuff and having a first channel through which the first tensile element passes, a second channel through which the second tensile element passes, a first anchor point to which the second end of the first tensile element is attached, and a second anchor point to which the second end of the second anchor point is attached, the first and second channels being formed within the rigid guide structure, and the first and second anchor points a being formed on outside surfaces of the rigid guide structure.

2. The body anchor of claim 1, wherein the cuff comprises a synthetic rubber material or an elastic fiber material.

3. The body anchor of claim 1, wherein the assistive device comprises a lower limb exoskeletal device, wherein the cuff is sized to be worn over a leg of the user.

4. The body anchor of claim 1, wherein the tensile elements are arranged about the cuff to counterbalance the load exerted by the assistive device.

5. The body anchor of claim 1, wherein the guide comprises:
    a first opening in a first end of an enclosure; and
    second and third openings in a second end of the enclosure opposite from the first end,
    wherein the first channel extends from the first opening to the second opening and the second channel extends from the first opening to the third opening.

6. The body anchor of claim 1, wherein the one or more tensile elements have loops at the second ends, wherein the one or more tensile elements pass through the loops and wrap around the cuff.

7. The body anchor of claim 1, wherein the cuff comprises a first end having a first plurality of openings and a second end having a second plurality of openings, wherein the one or more tensile elements are arranged through the first and second plurality of openings to force the first and second cuff ends together in proportion to the load exerted by the assistive device.

8. The body anchor of claim 7, wherein the one or more tensile elements are laced through the first and second plurality of openings.

9. The body anchor of claim 1, wherein the cuff comprises a non-isotropic material formed into a cylindrical structure, wherein the one or more tensile elements are arranged about the cylindrical structure to cause the circumference of the cylindrical structure to vary in proportion to a load exerted by the assistive device.

10. The body anchor of claim of 9 wherein the cuff comprises a first helically wound braid of fibers and a second helically wound braid of fibers, the first and second helically would braids of fibers being wound in opposite directions about the cylindrical structure.

11. An assistive device comprising:
    a prosthetic device;
    a compression cuff coupled to the prosthetic device, the compression cuff configured to be positioned around a body part of a user and to exert a compression force on a body part of a user, the compression force causing a frictional force between the compression cuff and the body part in order to mechanically couple the prosthetic device to the body part;
    one or more tensile elements each having:
        first ends mechanically coupled to the prosthetic device; and
        second ends, opposite the first ends, the second ends arranged about the compression cuff to cause the compression force to increase when a load exerted by the prosthetic device acts to displace the compression cuff from its position around the body part, wherein the one or more tensile elements comprise a first tensile element encircling the cuff in a first direction and a second tensile element encircling the cuff in a second direction opposite from the first direction, wherein the tensile elements are arranged to cause the compression force to increase at multiple points around a circumference of the cuff as the load increases, including at diametrically opposite points of the circumference.

* * * * *